United States Patent
Horne et al.

(10) Patent No.: US 11,110,044 B2
(45) Date of Patent: Sep. 7, 2021

(54) SKINCARE TREATMENT

(71) Applicant: Reckitt & Colman (Overseas) Limited, Slough (GB)

(72) Inventors: Rebecca Horne, Hull (GB); Diane Kelly, Hull (GB); Laurent Kirchhoffer, Ludwigshafen (DE); Richard Koontz, Hull (GB); James Young, Hull (GB)

(73) Assignee: RECKITT & COLMAN (OVERSEAS) HEALTH LIMITED, Slough (GB)

( * ) Notice: Subject to any disclaimer, the term of this patent is extended or adjusted under 35 U.S.C. 154(b) by 336 days.

(21) Appl. No.: 15/590,618

(22) Filed: May 9, 2017

(65) Prior Publication Data
US 2017/0246093 A1 Aug. 31, 2017

Related U.S. Application Data

(62) Division of application No. 12/811,705, filed as application No. PCT/GB2008/004283 on Dec. 24, 2008, now abandoned.

(30) Foreign Application Priority Data

Jan. 4, 2008 (GB) ...................................... 0800145

(51) Int. Cl.
| | | |
|---|---|---|
| *A61K 31/19* | (2006.01) | |
| *A61K 31/60* | (2006.01) | |
| *A61K 33/08* | (2006.01) | |
| *A61K 33/14* | (2006.01) | |
| *A61K 33/06* | (2006.01) | |
| *A61P 17/10* | (2006.01) | |
| *A61K 8/36* | (2006.01) | |
| *A61Q 19/00* | (2006.01) | |
| *A61K 8/368* | (2006.01) | |
| *A61K 45/06* | (2006.01) | |

(52) U.S. Cl.
CPC ............... *A61K 8/36* (2013.01); *A61K 8/368* (2013.01); *A61K 31/60* (2013.01); *A61K 33/06* (2013.01); *A61K 45/06* (2013.01); *A61Q 19/00* (2013.01); *A61K 2800/242* (2013.01); *A61K 2800/31* (2013.01); *A61K 2800/88* (2013.01)

(58) Field of Classification Search
CPC .......... A61K 8/36; A61K 31/19; A61K 31/60; A61K 33/06; A61K 33/08; A61K 33/14; A61P 17/10
See application file for complete search history.

(56) References Cited

U.S. PATENT DOCUMENTS

| | | | |
|---|---|---|---|
| 3,663,716 A | 5/1972 | Stolar | |
| 4,318,907 A * | 3/1982 | Kligman | A61K 8/368 514/164 |
| 4,379,143 A | 4/1983 | Sherry et al. | |
| 4,822,604 A | 4/1989 | Knoll et al. | |
| 5,221,534 A | 6/1993 | DesLauriers et al. | |
| 5,612,324 A * | 3/1997 | Guang Lin | A61K 8/368 514/159 |
| 5,955,067 A | 9/1999 | Oge et al. | |
| 2004/0208902 A1 | 10/2004 | Gupta | |

FOREIGN PATENT DOCUMENTS

| | | | |
|---|---|---|---|
| EP | 1393715 A1 | 3/2004 | |
| JP | 2001187741 A | 7/2001 | |
| WO | 0103619 A1 | 1/2001 | |
| WO | 02060408 A1 | 8/2002 | |
| WO | 2005030160 A1 | 4/2005 | |
| WO | WO2009087354 | * | 7/2009 |

OTHER PUBLICATIONS

International Search Report issued in related application No. PCT/GB2008/004283 dated Oct. 13, 2009.
Kubo, I. et al. "Naturally Occurring Antiacne Agents," Journal of Natural Products, 1994, pp. 9-17, 57(1).
Togashi, N. et al., "Antibacterial Activity of Long-Chain Fatty Alcohols against *Staphylococcus aureus*," Molecules, 2007, pp. 139-148, vol. 12.
Anonymous: "Acne-prone skin: Oil-free lotion," Goodskin, Mar. 2005 (Mar. 1, 2005), XP002514811, Retrieved from the Internet <URL:http://www.goodskindermcare.com/templates/products/sp_nonshaded.tmpl?CATEGORY_ID=CATEGORY6769&PRODUCT_ID=PROD6918> [retrieved on Feb. 10, 2009].
Anonymous: "'Warming Anti-Blackhead Cream Cleanser," BIORE, Sep. 2006 (Sep. 1, 2006), XP002514810, Retrieved from the Internet <URL:http://www.biore.com/usa/products/productinfo.asp?productID=3> [retrieved on Feb. 10, 2009].
Database WPI Week 200170, Derwent Publications Ltd., London, GB; AN 2001-609227, XP002514812.

\* cited by examiner

*Primary Examiner* — Jeffrey S Lundgren
*Assistant Examiner* — Chris E Simmons
(74) *Attorney, Agent, or Firm* — Troutman Pepper Hamilton Sanders LLP; Ryan Schneider; Chris N. Davis

(57) ABSTRACT

The invention relates to a method of treating acne by the topical administration of an acne active ingredient in the presence of a) an anhydrous composition comprising a component that in the presence of water generates heat, and b) water. The invention also relates to an acne treatment kit comprising a first composition which is anhydrous and comprises a component that in the presence of water generates heat on the skin to which it is applied and a second composition which comprises an aqueous carrier, at least one of said compositions comprising an acne active ingredient, said compositions being stored in isolation from each other and being capable of generating heat when they are combined.

18 Claims, 2 Drawing Sheets

SKINCARE TREATMENT

CROSS-REFERENCE TO RELATED APPLICATIONS

This application is a divisional application of, and claims priority to, U.S. patent application Ser. No. 12/811,705, filed 30 Nov. 2010, which is a U.S. National Stage of International Application No. PCT/GB2008/004283, filed 24 Dec. 2008, which claims the benefit of GB 0800145.5, filed 4 Jan. 2008, the disclosures of all of which are herein incorporated by reference in their entirety.

BACKGROUND OF THE INVENTION

1. Field of the Invention

The present invention relates to a method of treating acne, to an acne treatment kit, to compositions and kits useful in such methods and to processes to prepare said composition and/or kits.

2. Background of Related Art

Acne vulgaris (acne) is a chronic inflammatory condition of the pilosebaceous units of the skin, which is particularly prevalent in adolescents. The condition generally causes the formation, on the skin, of comedones, red papules, pustules and sometimes cysts. This is unsightly and furthermore, if untreated, acne can lead to scarring of the skin. The major causes of acne are thought to be an increase in sebum production, an increased presence of *Propionibacterium acne* (*P. acne*), blockage of the pilosebaceus duct and the production of inflammation.

Remedies for the topical treatment of acne generally provide for the application to the affected area of a skincare composition comprising at least one ingredient effective to treat acne. Such actives include the classes of topical retinoids, antibiotics, anti-bacterials and keratolytic agents, for example tretinoin, adapalene, tazarotene, clindamycin, erythromycin, azelaic acid, benzoyl peroxide and salicylic acid.

It has now been found that an improved acne treatment may be achieved by the topical administration of an acne active ingredient in the presence of a component that generates heat on the skin.

It has been found that the above treatment provides improved efficacy in the topical treatment of acne. For example, factors including improved sebum removal and improved pore cleansing may lead to a reduction in the number and intensity of acne lesions.

Accordingly, the present invention provides a method of treating acne comprising the topical administration of an acne active ingredient in the presence of:
a) an anhydrous composition comprising a component that in the presence of water generates heat on the skin, and
b) water.

BRIEF SUMMARY OF THE INVENTION

As specified in the Background Section, there is a great need in the art to develop novel topical treatments for acne. The present invention satisfies this and other needs. Embodiments of the present invention relate generally to topical administration of an acne active ingredient in the presence of a component that generates heat on the skin.

In one aspect, the invention provides a method of treating acne by the topical administration of an acne active ingredient in the presence of: an anhydrous composition comprising a component that in the presence of water generates heat on skin, and an aqueous composition.

In another aspect, the invention provides a method of treating acne comprising: mixing a skincare formulation; and applying the skincare formulation to skin, wherein the skincare formulation comprises: an anhydrous composition; an aqueous composition; at least one acne active ingredient; and a component that in the presence of water generates heat.

In another aspect, the invention provides a method of treating acne comprising: applying a skincare formulation to skin; and mixing the skincare formulation on the skin, wherein the skincare formulation comprises: an anhydrous composition; an aqueous composition; at least one acne active ingredient; and a component that in the presence of water generates heat.

In yet another aspect, the invention provides a method of treating acne comprising: applying a first composition to skin; applying a second composition to the skin; and mixing the first and second compositions, wherein the first composition comprises an anhydrous composition comprising a component that in the presence of water generates heat on skin; wherein the second composition comprises an aqueous composition; and wherein at least one of the first and second compositions comprises at least one acne active ingredient.

In an embodiment of any of the above methods, the administration of the anhydrous composition and the aqueous composition is substantially simultaneous. In another embodiment of any of the above methods, the administration of the anhydrous composition and the aqueous composition is sequential.

In an embodiment of any of the above methods, the acne active ingredient is present in the anhydrous composition. In another embodiment of any of the above methods, the acne active ingredient is present in the aqueous composition. In yet another embodiment of any of the above methods, the acne active ingredient is present in both the anhydrous composition and the aqueous composition.

In an embodiment of any of the above methods, the acne active ingredient is a keratolytic agent.

In an embodiment of any of the above methods, the acne active ingredient is present in an amount of from 0.1% to 10% by weight of the combined anhydrous and aqueous compositions.

In another embodiment of any of the above methods, the acne active ingredient is present in an amount of 0.1% to 5% by weight of the anhydrous composition.

In another embodiment of any of the above methods, the acne active ingredient is present in an amount of 0.1% to 5% by weight of the aqueous composition.

In an embodiment of any of the above methods, the component activatable by water to generate heat on the skin is selected from the group consisting of zeolites and bivalent metal halides.

In an embodiment of any of the above methods, the component activatable by water to generate heat on the skin is magnesium chloride.

In an embodiment of any of the above methods, the anhydrous composition comprises from 5% to 60% by weight of said component that generates heat in the presence of water.

In an embodiment of any of the above methods, the anhydrous composition comprises an anhydrous carrier. In another embodiment of any of the above methods, the anhydrous carrier comprises a hydrocarbon material. In one specific embodiment of any of the above methods, the anhydrous carrier comprises mineral oil.

In an embodiment of any of the above methods, the anhydrous composition comprises a surfactant. In another embodiment of any of the above methods, the surfactant is selected from the group consisting of alkyl sulphates, alkyl ether sulphates, alpha-olefin sulphates, alkylsarcosinates and aryl-sulphonated derivatives thereof. In one specific embodiment of any of the above methods, the surfactant is selected from the group consisting of sodium lauryl sulphate and sodium dodecyl sulphate.

In an embodiment of any of the above methods, the anhydrous composition comprises from 1% to 10% by weight surfactant.

In an embodiment of any of the above methods, the aqueous composition is a cleansing composition comprising a surfactant.

In an embodiment of any of the above methods, the aqueous composition is water.

In an embodiment of any of the above methods, the anhydrous composition and aqueous composition are contained within a package as described herein.

These and other objects, features and advantages of the present invention will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below.

DETAILED DESCRIPTION OF THE INVENTION

Figure 1:
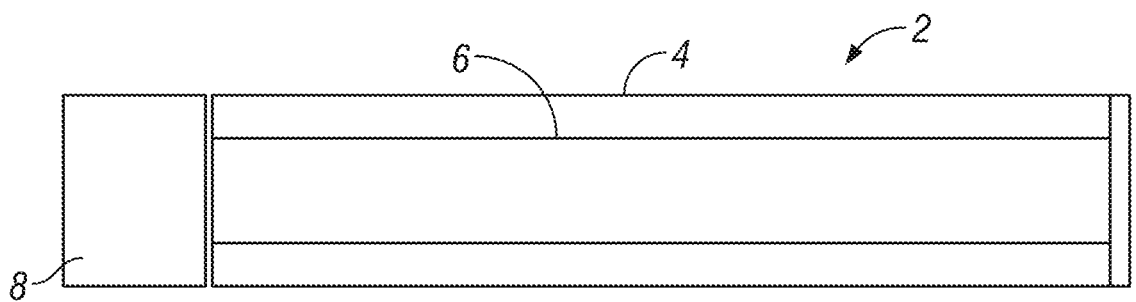
FIG. 1 shows a side view of a package comprising an inner tube containing a first composition located within a clear outer tube containing a second composition.

As specified in the Background Section, there is a great need in the art to develop novel topical treatments for acne. The present invention satisfies this and other needs. Embodiments of the present invention relate generally to topical administration of an acne active ingredient in the presence of a component that generates heat on the skin.

Definitions

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

Where reference is made herein to an anhydrous composition, this means a composition which is substantially free of water; for example, it will contain less than 2% by weight water preferably less than 1% by weight water and most preferably less than 0.1% by weight water.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

Methods and Compositions of the Invention

The present invention provides a method of treating acne comprising the topical administration of an acne active ingredient in the presence of
 a) an anhydrous composition comprising a component that in the presence of water generates heat on the skin, and
 b) water or an aqueous composition.

In another aspect the present invention also provides an acne treatment kit comprising a first composition which is anhydrous and comprises a component that in the presence of water generates heat and a second composition which comprises an aqueous carrier, at least one of said compositions comprising an acne active ingredient, said compositions being stored in isolation from each other and being capable of generating heat when they are combined.

In a yet further aspect the present invention provides a skincare formulation obtained by mixing on, or prior to application to, the skin comprising
 a) a first composition which is anhydrous and comprises a component that in the presence of water generates heat;
 b) a second composition which comprises an aqueous carrier; and
 c) at least one acne active ingredient.

In still a further aspect the present invention provides an anhydrous composition for the treatment of acne comprising an acne active ingredient, a component that in the presence of water generates heat and a carrier therefor.

The invention also provides an acne treatment package for dispensing a first and a second composition onto the skin, said first composition being anhydrous and comprising a component that in the presence of water generates heat and said second composition comprising an aqueous component, at least one of said compositions comprising an acne active ingredient, wherein said package comprises a first chamber and a second chamber, each of said first and second chambers having an outlet, wherein said first composition is stored in said first chamber and said second composition is stored in said second chamber, said compositions being stored in isolation from each other and the package being arranged such that said first and second compositions are combined after passing though each respective outlet.

The invention also provides a process of dispensing an acne treatment onto the skin comprising the application to the skin of a first composition which is anhydrous and comprises a component that in the presence of water generates heat, and a second composition which comprises an aqueous carrier, at least one of said compositions comprising an acne active ingredient, and mixing said compositions to generate heat on the skin.

The invention also provides a process to prepare an acne treatment kit comprising inserting a first composition which is anhydrous and comprises a component that in the presence of water generates heat into a first chamber of a multi-chambered package and inserting a second composition which comprises an aqueous carrier into a second chamber of said package, at least one of said compositions comprising an acne active ingredient, and providing means for combining said compositions on, or prior to application to, the skin.

In a method according to the invention, an acne active ingredient is applied to the skin in the presence of an anhydrous composition comprising a component that in the presence of water generates heat and water. The heat is generated on the skin and is useful to raise the temperature on the surface of the skin. The amount of heat-generating component present in the anhydrous composition is a level that the heat generated by the combination of the anhydrous composition with the water is acceptable on the skin of a user and does not burn the skin.

In accordance with the present invention, the anhydrous composition may be applied to the skin and water applied thereto. The water may be applied before, at the same time as, or after the application of the anhydrous composition. Preferably the anhydrous composition and water are combined by rubbing the ingredients together. In this way the heat generating component is most effectively combined with water to provide a heating effect on the skin.

The water may be obtained from any suitable source, for example a water tap. The water may also be provided in an aqueous composition which may include one or more additional ingredients, especially skincare ingredients. There may be sufficient water already present on the skin to produce a suitable heating effect if the anhydrous composition is rubbed into the skin with sufficient vigour.

Preferably, the aqueous composition forms part of a package in combination with the anhydrous composition, which allows a measured amount of water to be applied to the skin thus allowing more control of the heating effect.

In one embodiment, the administration of the anhydrous composition and the aqueous composition on the skin is substantially simultaneous. The anhydrous composition and aqueous composition may be combined just prior to application to the skin or they may be combined on the skin. For example, the anhydrous composition and aqueous composition may be dispensed from separate chambers within a package. The outlet of each chamber may allow the compositions to be applied directly onto the skin and then combined by the user rubbing the compositions on the surface of the skin or the compositions may be combined as they pass through a dispensing nozzle before application to the skin.

A skincare formulation is provided when said anhydrous composition is combined with water. Heat is generated on the skin which enhances the effect of the acne active ingredient. The skincare formulation may be left on the skin in which case the heat generated will gradually subside. Preferably the composition is rinsed off the skin, leaving a therapeutically effective amount of the acne active ingredient on the skin.

The acne active ingredient may be present separate from the anhydrous composition or the aqueous composition, it may be present in either the anhydrous and aqueous compositions, or it may be present in both the anhydrous and aqueous compositions.

The acne active ingredient may be selected from any class of materials that are effective to treat acne, including topical retinoids, antibiotics, anti-microbials, anti-bacterials, anti-inflammatory agents and keratolytic agents, for example tretinoin, adapalene, tazarotene, clindamycin, erythromycin, azelaic acid, benzoyl peroxide, hydrogen peroxide and salicylic acid. If desired, two or more acne active ingredients may be employed. The active ingredients may be present in the same or in different compositions.

The active ingredient is present in the formulation in a therapeutically effective amount, as generally known in the art. For most active ingredients, a range from 0.001% to 10% by weight, especially from 0.1% to 10% by weight, could be expected. Thus, generally each composition may comprise the above recited amount of acne active ingredient. Preferably, an acne active ingredient is present in an amount of 0.1% to 5% by weight of the anhydrous composition. Further preferably, an acne active ingredient is present in an amount of 0.1% to 5% by weight of the aqueous composition. However, it may be a benefit to reduce the total amount of any one active in the anhydrous or aqueous compositions, or to separate a plurality of actives, by including at least one acne active ingredient in both compositions. Thus, in a preferred embodiment, an acne active ingredient is present in an amount from 0.1% to 5% by weight of both aqueous and anhydrous compositions.

In one embodiment, said acne active ingredient is a keratolytic agent such as salicylic acid. Salicylic acid is preferably incorporated into the composition according to the invention as the free acid. However, the pH of the composition may, and generally will, be such that the salicylic acid exists in the composition in dissociated form. As the composition may well contain cationic counterions, the salicylic acid may then be thought of as being present in salt form. Alternatively, the salicylic acid may be incorporated into the composition in salt form, e.g., as a salt with a Group I metal, such as sodium salicylate. As used herein, unless the context requires otherwise, any and all references to salicylic acid should be taken to encompass references to the acid and to dissociated forms and salts thereof.

The total concentration of salicylic acid in the formulation according to the invention, i.e., the combined anhydrous and aqueous compositions, is preferably at least 0.1% by weight, more preferably at least 0.5% by weight, most preferably at least 1.0% and especially at least 1.5% by weight. The concentration of salicylic acid is preferably less than 10% by weight, more preferably less than 6% by weight, and most preferably less than 4% by weight. Conveniently, the total concentration of salicylic acid may fall in the range 0.1% to 10% by weight, preferably 0.5% to 10% by weight, more preferably 1.0% to 6%, and most preferably 1.5% to 4.0% by weight. A particularly preferred total concentrations of salicylic acid is approximately 1.5-2% by weight of the composition.

In one embodiment, said acne active ingredient, preferably salicylic acid, is present in the anhydrous and aqueous compositions. The amount of acne active ingredient may be different in each composition. However, preferably, the aqueous composition comprises from 0.5% to 4% by weight, more preferably 1% to 3% by weight, acne active ingredient. Further preferably, the anhydrous composition comprises from 0.5% to 4% by weight, more preferably 1% to 3% by weight, acne active ingredient.

In accordance with the invention, any pharmaceutically acceptable component that generates heat in the presence of water may be used. Preferred examples are selected from the group of materials that generate heat within the classes of zeolites (aluminosilicates); metal halides, sulphates, carbonates and oxides; and polyhydric alcohols. Preferred classes of materials include zeolites and bivalent metal halides. These materials are well known to those skilled in the art. Examples of bivalent metal halides and oxides may include magnesium chloride, iron chloride, zinc chloride, magnesium oxide, calcium oxide, magnesium sulphate and calcium chloride.

Such heat generating materials will suitably be present in the anhydrous composition in an amount to heat the skin to facilitate opening and cleansing of the pores. For example, such materials may be used in an amount of up to 70% by weight of the anhydrous composition, for example, from 1% to 70% by weight, preferably from 1% to 40% by weight, more preferably from 1% to 25% by weight and most preferably from 1% to 15% by weight.

The person skilled in the art will appreciate that the heat generated must be less than that which will cause heat damage to the skin. Preferably the temperature of the skin is raised by no more than 50° C. In order to be effective, preferably, the temperature of the skin is raised by at least 2° C., more preferably at least 10° C. Conveniently, the temperature of the skin may be raised to a temperature in the range 4° C. to 70° C., preferably 4° C. to 15° C.

Preferably, the component that in the presence of water generates heat comprises a bivalent metal halide, further preferably a metal halide selected from magnesium chloride, iron chloride, zinc chloride and calcium chloride, most preferably magnesium chloride.

In one embodiment of the invention, the anhydrous composition comprises from 5% to 60% by weight, preferably from 10% to 50% by weight, more preferably from 12% to 40% by weight and most preferably from 15% to 35% by weight of said water-activatable, heat-generating component.

In accordance with the invention, the anhydrous composition comprises an anhydrous carrier. Conveniently, this may be an oily material. A physiologically effective oil useful in accordance with the present invention may be any cosmetically and/or dermatologically acceptable synthetic or natural oil known to the person skilled in the art. Such oils may also provide emollient properties on the skin, for example to maintain the soft, smooth and pliable appearance of the skin. Suitable ingredients include hydrocarbons, silicone oils, triglycerides, waxes, fatty acids, fatty acid alcohols and esters thereof, mineral oils, vegetable oils and hydrogenated vegetable oils, lanolin or mixtures thereof. Examples of hydrocarbons include paraffins (for example paraffinum liquidum and white soft paraffin), petrolatum, hydrogenated polyisobutene, alkyl benzoates, isohexadecane, isododecane, isononyl isonanoate, diisopropylcyclohexane; examples of silicone oils include dimethicone, cyclomethicone or cetyldimethicone; examples of triglycerides include natural triglycerides and synthetic or semi-synthetic triglycerides; examples of waxes include vegetable waxes such as carnauba wax, animal waxes such as beeswax, and mineral waxes such as paraffin wax, ozokerite; examples of esters of fatty acids or alcohols include isopropyl palmitate, isopropyl myristate, dioctylmaleate, glyceryl oleate and cetostearyl isononanoate, octyl palmitate; examples of mineral oils include Vaseline oil; examples of vegetable oils include jojoba oil, soy bean oil, coconut oil, sunflower seed oil, apricot kernel oil, shea butter, avocado oil and examples of hydrogenated vegetable oils include hydrogenated palm oil.

Such materials may be used in an amount greater than 30% by weight, more preferably greater than 35% by weight, advantageously greater than 40% by weight and most preferably greater than 45% by weight of the composition. The carrier generally provides the largest component by weight of the anhydrous composition. Preferably, the anhydrous composition comprises from 30% to 99% by weight, preferably from 35% to 95% by weight, more preferably from 40% to 90% by weight and most preferably from 50% to 85% by weight of said carrier.

In one embodiment, the anhydrous carrier comprises a mineral oil. Preferably, the mineral oil is blended with a styrene copolymer, for example a hydrogenated alkylene-styrene copolymer, more preferably a hydrogenated butylene/ethylene/styrene copolymer or a hydrogenated ethylene/propylene/styrene copolymer or a mixture thereof. A particularly preferred source of a mineral oil/styrene copolymer blend is available under the tradename Versagel from Penreco, 138 Petrolia Karns City USA. Preferably, mineral oil is combined with a hydrogenated alkylene-styrene copolymer/mineral oil blend.

In preferred compositions which comprise mineral oil, the total mineral oil is preferably present in an amount from 50% to 85% by weight, more preferably from 60% to 80% by weight, of the anhydrous composition; conveniently this may be a blend comprising mineral oil in an amount from 25% to 60% by weight (more preferably from 35% to 50% by weight) and a mineral oil/styrene copolymer blend in an amount from 20% to 40% by weight (more preferably from 24% to 32% by weight).

In another embodiment, the anhydrous composition comprises a surfactant. This forms a particularly preferred aspect of the present invention as it provides a composition with advantageous viscosity and skin-feel properties. For example, it may provide a less oily feel to the composition so that it is more pleasant to apply and retain on the skin. For example, a greasy and/or oily and/or sticky feel on the skin may be reduced. In particular, the inclusion of a surfactant in a composition where the carrier is a hydrocarbon (such as mineral oil) improves the aesthetic feel of the composition on the skin. In this way, it has been found that less expensive carriers may be employed in the anhydrous composition. Furthermore, the anhydrous composition has good viscosity properties as it is not too viscous to apply and does not run off the skin when applied thereto. A suitable viscosity is that of a thickened liquid such that it is thicker than water and preferably remains in the area to which it is applied, even when the user moves or applies it to a non-horizontal skin surface. It is a preferred feature of the invention that the compositions have a viscosity which allows them to be dispensed conveniently from a package, especially through a dispensing nozzle. The viscosity range values of such compositions will be known to those skilled in the art. The inclusion of at least one surfactant may provide that it may not be necessary to include a thickening component in the composition.

In one embodiment, the anhydrous composition comprises a surfactant and does not include a thickening component.

The surfactant may be an anionic, non-ionic, cationic and zwitterionic/amphoteric surfactant. Any conventionally used pharmaceutically and cosmetically acceptable surfactant may be used and these will be known to the person skilled in the art. Examples of non-ionic surfactants include the class of ethoxylated fatty alcohols and other surfactants such as oleth-5, PEG-5 cocamide, polysorbate 20, PEG-40 hydrogenated castor oil, alkyl poly(ethylene oxide), copolymers of poly(ethylene oxide) and poly(propylene oxide) (commercially called Poloxamers or Poloxamines), alkyl polyglucosides, including: octyl glucoside, decyl maltoside, fatty alcohols, cetyl alcohol, oleyl alcohol; examples of anionic surfactants includes the class of alkyl ether sulphates, such as sodium lauryl sulphate, sodium laureth sulphate, sodium dodecyl sulfate, ammonium lauryl sulfate, ammonium laureth sulphate, sodium C12-15 pareth sulphate and disodium laureth sulfosuccinate, soaps or fatty acid salts; examples of cationic surfactants include cationic modified guar, alkyltrimethylammonium salts, for example cetrimonium chloride, cetyl trimethylammonium bromide, cetylpyridinium chloride, polyethoxylated tallow amine, benzalkonium chloride, benzethonium chloride and behentrimonium chloride; examples of amphoteric surfactants include the class of alkylamido alkyl amines and dodecyl betaine, dodecyl dimethylamine oxide, cocamidopropyl betaine, cocamidopropyl hydroxysultaine, sodium lauroamphoacetate, cocoamphoglycinate or sodium cocoamphoacetate. A further preferred group of classes of surfactants are alkyl sulphates, alkyl ether sulphates, alpha-olefin sulphates, alkylsarcosinates and aryl-sulphonated derivatives thereof.

Preferably, the surfactant comprises an anionic surfactant, optionally in combination with other surfactants. Most preferably, the surfactant comprises an alkali metal sulphate, such as sodium lauryl sulphate and/or sodium dodecyl sulphate.

Preferably, when present, the anhydrous composition comprises from 1-20% by weight surfactant, further preferably from 1% to 10% by weight, more preferably from 3% to 15% by weight and most preferably from 4% to 10% by weight surfactant.

In one embodiment, the present invention provides an anhydrous composition comprising:
(a) 1% to 5% by weight salicylic acid;
(b) 10% to 35% by weight magnesium chloride;
(c) 4% to 10% by weight surfactant; and
(d) 50% to 85% by weight carrier.

Further preferably, the anhydrous composition consists essentially of the above ingredients.

In one embodiment of the present invention, the aqueous composition is a cleansing composition comprising a surfactant. The surfactant may be an anionic, non-ionic, cationic and zwitterionic/amphoteric surfactant. Any conventionally used pharmaceutically and cosmetically acceptable surfactant may be used and these will be known to the person skilled in the art. Particular surfactants may be as described above with respect to the anhydrous composition. Preferably, the surfactant comprises an anionic surfactant and/or a non-ionic surfactant. Preferred materials include lauryl or laureth sulphates (such as sodium or triethanolamine lauryl/laureth sulphates) and polypropyleneglycols, polyethylene glycols and derivatives thereof.

In preferred compositions, it is desired that the total surfactant concentration in the aqueous and anhydrous compositions when combined to provide the formulation, is sufficient such that when rubbed into the skin, a foam is produced which can be rinsed off the skin.

The aqueous and anhydrous compositions may also include other skincare ingredients as desired, such as for example, emollients, humectants, film formers, cooling agents, soothing agents, anti-inflammatories.

In particular, the anhydrous and aqueous compositions may also comprise thickening agents which increase the viscosity of the composition. Examples include polyethylene glycols; polyoxyethylene cetyl ethers; Acrylates/Vinyl Isodecanoate crosspolymer, polyamide resins such as Sylvaclear (tradename), lanolin, stearyl alcohol and salt.

In one embodiment, the present invention provides an aqueous composition comprising:
(a) 1% to 5% by weight salicylic acid;
(b) 5% to 85% by weight surfactant; and
(c) 10% to 94% by weight water.

Further preferably, the aqueous composition consists essentially of the above ingredients.

Preferably, when present, the anhydrous and/or aqueous compositions comprise from 1-20% by weight thickener, more preferably from 2% to 15% by weight, and most preferably from 3% to 10% by weight thickener.

The aqueous and anhydrous compositions provided in accordance with the present invention are suitably in the form of a liquid or a gel, preferably as a viscous liquid.

In accordance with the present invention, the anhydrous and aqueous compositions may comprise other conventional ingredients, such as anti-microbial agents, sequestering agents, colouring agents and perfumes. Such ingredients and the amounts in which they are incorporated in the composition are within the knowledge of those skilled in the art.

The present invention also provides an acne treatment package for storing and dispensing the above described aqueous and anhydrous compositions onto the skin. The package comprises a first chamber and a second chamber, each chamber having an outlet thereto, wherein said anhydrous composition is stored in said first chamber and said aqueous composition is stored in said second chamber, said compositions being stored in isolation from each other and being arranged to be combined after passing though said respective outlets onto the skin. On combination of the compositions, heat is generated, effective to raise the temperature of the skin.

In expelling a portion of the contents of the package, each composition passes through the outlet of the chamber in which it is stored. The outlets may be adjacent so that on expelling the compositions from the package at the same time, they may be combined after they pass through the outlets onto the skin. It may be desired, however, to expel the compositions separately, for example to apply one composition and then target the second composition in the area of the first composition. In this case it is not necessary that the outlets of each chamber are near to each other. Although a heating effect is obtained as soon as the water comes into contact with the component that generates heat on contact with water, it is preferred to mix the compositions by rubbing them into the skin.

In one embodiment, the package further comprises a dispensing nozzle through which the combined compositions are dispensed onto the skin. The aqueous and anhydrous compositions may be combined in the dispensing nozzle or a chamber leading thereto and then targeted onto the affected area of the skin.

In one embodiment, the package comprises a receptacle partitioned into first and second chambers. Preferably, the package comprises a dispensing nozzle in which the aqueous and anhydrous compositions may be combined before being expelled onto the skin.

In another embodiment, the package comprises a tube comprising an anhydrous or aqueous composition and an inner tube comprising the other of said anhydrous or aqueous composition. Suitably, the inner tube is encompassed within an outer tube which forms the packaging.

Preferably, the package is squeezable to expel said anhydrous or aqueous compositions.

It will be appreciated that a method according to the invention, including a method of treating acne comprising the topical administration of an acne active ingredient in the presence of a component that in the presence of water generates heat, may be a therapeutic method, but will often be a primarily cosmetic method, the objective of which is to reduce or eliminate externally visible, and often unsightly, symptoms of acne.

Referring firstly to FIG. 1, an acne treatment package (2) for dispensing first and second compositions onto the skin comprises an outer tube (4) which provides a first chamber and an inner tube (6) which provides a second chamber, the contents of the first chamber being isolated from the second chamber. The outer tube has a cap (8).

An aqueous composition which comprises an acne active ingredient is stored in said first (outer) chamber and an anhydrous composition which comprises an acne active ingredient and a component that in the presence of water generates heat on the skin is stored in said second (inner) chamber.

In another embodiment, the anhydrous composition is present in the outer tube and the aqueous composition is present in the inner tube.

In a further embodiment, the acne active ingredient is present in either one of, or both of, the anhydrous or aqueous compositions.

In a further embodiment, at least one surfactant is present in either one of, or both of, the anhydrous and aqueous compositions.

Figure 2:
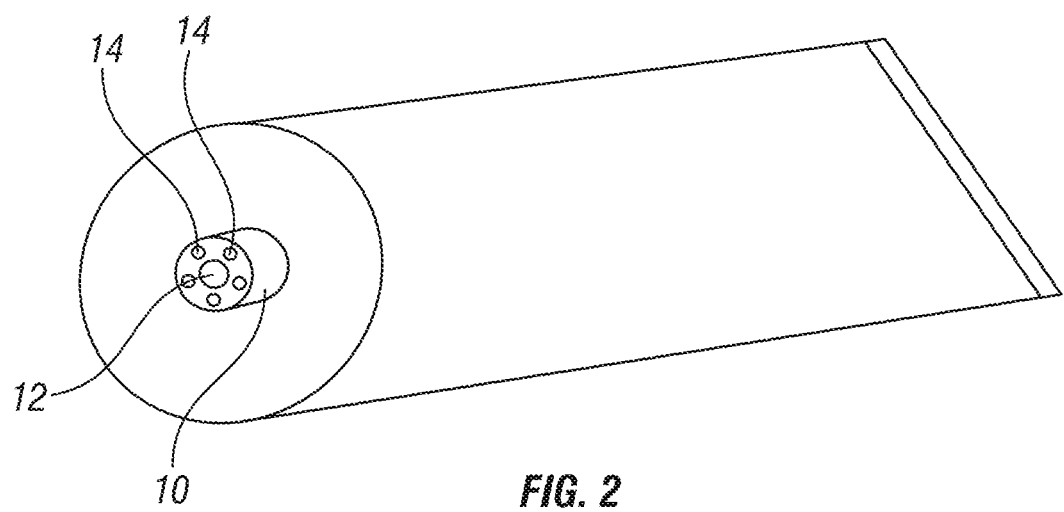
FIG. 2 shows a perspective view of one end of a tube comprising a first dispensing nozzle.

Referring to FIG. 2, the package comprises a neck which forms a dispensing nozzle (10). The inner tube has an outlet leading into a central channel (12) of the dispensing nozzle. The outer tube has an outlet leading to a plurality of openings (14) around the periphery of the dispensing nozzle.

In use, the dispensing nozzle (10) is placed on or near the affected area of the skin and the outer and inner tubes squeezed simultaneously. The anhydrous composition is expelled through the central channel (12) and the aqueous composition is expelled from the plurality of openings (14). As the compositions are expelled from the package they are combined as they pass onto the skin. The combined compositions are rubbed together into the skin which causes heat to be generated. The combined formulation is then rinsed from the skin.

Figure 3:
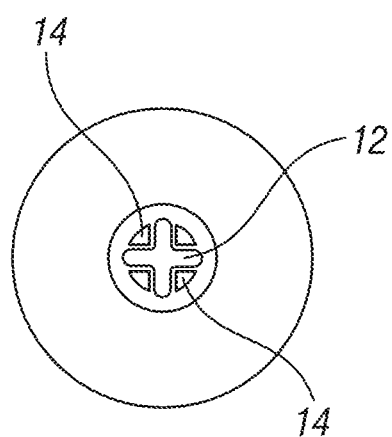
FIG. 3 shows an end view of a second dispensing nozzle.

FIG. 3 shows an embodiment where the central passage (12) is enlarged towards the periphery of the dispensing nozzle and allows a greater amount of the composition in the inner tube to be expelled at a given time in relation to the amount of composition expelled from the openings (14) in the outer tube.

Figure 4:
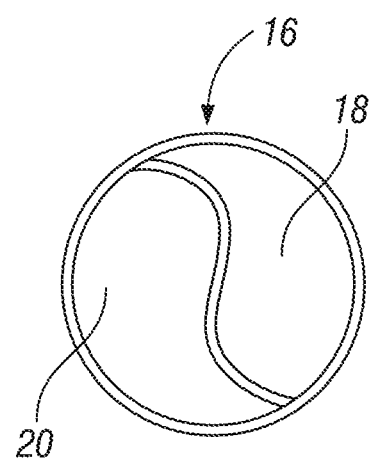
FIG. 4 shows a sectional view of a partitioned package comprising first and second chambers.

FIG. 4 shows a section view of a partitioned package (16) providing first (18) and second (20) chambers. The anhydrous composition is stored in the first chamber (18). The aqueous composition is stored in the second chamber (20).

Figure 5:
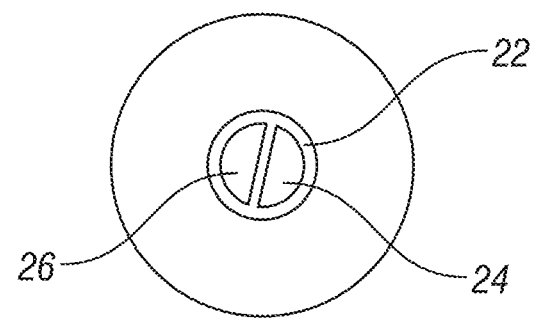
FIG. 5 shows an expanded perspective view of the dispensing nozzle from a partitioned package.

FIG. 5 shows a perspective view of one end of the partitioned package (16) which is in the form of a tube. The package comprises a neck which forms a dispensing nozzle (22). The dispensing nozzle is divided down the middle to form two semi-circular channels. A first channel connects the first chamber (18) with a dispensing aperture (24). A second channel connects the second chamber (20) with a dispensing aperture (26).

When it is desired to apply the combined compositions to the skin, the dispensing nozzle (10) is placed on or near the affected area of the skin and the tube (16) squeezed. The anhydrous composition is expelled from the aperture (24) and the aqueous composition is expelled from the aperture (26). As the compositions are expelled from the package they are combined as they pass onto the skin. The combined compositions are rubbed together into the skin which causes heat to be generated. The combined formulation is then rinsed from the skin.

In the following examples, there are described several preferred embodiments to illustrate the invention. However, it is to be understood that the invention is not to be limited to the specific embodiments.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

In the examples, the ingredients are available as follows:

Carrier[1] is a blend of mineral oil and ethylene/propylene/styrene copolymer and butylene/ethylene/styrene copolymer is available from Penreco under the trade name Versagel M-1600. Carrier[2] is a blend of mineral oil and ethylene/propylene/styrene copolymer and butylene/ethylene/styrene copolymer and is available from Penreco under the trade name Versagel R-500. Thickener[1] is a combination of Glyceryl Dibehenate, Tribehenin and Glyceryl Behenate and is available from Gattefosse under the tradename Compritol ATO 888. Thickener[2] is polyoxyethylene cetyl ether available under the tradename Brij 56. Acrylates/Vinyl Isodecanoate crosspolymer is available from 3V under the tradename Stabylen-30. The polyamide resin is available from Arizona Chemical under the tradename Sylvaclear AF1900V. Triethanolamine laureth sulphate (TEA-LS) is available under the tradename Sunform-T7. Cocamidopropyl betaine is available under the trade name Incronam 30. PEG-150 is available under the tradename Crothix liquid. PEG-150 Pentaerythrityl Tetrastearate is available from Crothix.

Any one of the heating compositions illustrated below may be combined with any of the aqueous compositions illustrated below. The compositions are rubbed together on the skin and after a desired period may be rinsed off.
Heating Compositions The ingredients listed in each example below were combined by mixing according to conventional methods.

Examples 1-4

| | Examples | | | |
|---|---|---|---|---|
| Materials | 1 | 2 | 3 | 4 |
| Carrier[1] | 38.5% | 38.5% | — | — |
| Carrier[2] | — | — | 38.5% | 38.5% |
| Light Mineral oil | 45% | 45% | 45% | 45% |
| Salicylic acid | 1.5% | 1.5% | 1.5% | 1.5% |
| $MgCl_2$ | 15% | — | 15% | — |
| Zeolite | — | 15% | — | 15% |

Examples 5-10

| | Examples | | | | | |
|---|---|---|---|---|---|---|
| Materials | 5 | 6 | 7 | 8 | 9 | 10 |
| Carrier[2] | 38.5% | 25% | 15.5% | 15.5% | — | 13% |
| Light Mineral oil | 25% | 31.8% | 60% | 60% | 33.5% | 35% |
| Salicylic acid | 1.5% | 1.5% | 1.5% | 1.5% | 1.5% | 1.5% |
| Butylene glycol | 20% | 26.7% | — | — | 30% | 15.5% |
| Thickener[1] | — | — | 8% | 8% | — | — |
| $MgCl_2$ | 15% | 15% | — | 15% | — | — |
| Zeolite | — | — | 15% | — | 15% | 15% |
| PEG-8 | — | — | — | — | 10% | 10% |
| Thickener[2] | — | — | — | — | 10% | 10% |

Examples 11-14

| | Examples | | | |
|---|---|---|---|---|
| Materials | 11 | 12 | 13 | 14 |
| Carrier[2] | 13.5% | 13.5% | 7% | — |
| Light Mineral oil | — | — | 68.5% | 60.5% |
| Salicylic acid | 1.5% | 1.5% | 1.5% | 1.5% |
| Butylene glycol | 50% | 45% | — | — |
| Thickener[1] | — | — | 8% | 8% |
| Zeolite | 15% | 30% | 15% | 30% |
| PEG-8 | 10% | 5% | — | — |
| Brij 56 | 10% | 5% | — | — |

Examples 15-17

| | Examples | | |
|---|---|---|---|
| Materials | 15 | 16 | 17 |
| Salicylic acid | 1.5% | 1.5% | 1.5% |
| Butylene glycol | 40% | 26% | 25% |
| Glycerine | 26% | 40% | 40% |
| Acrylates/Vinyl Isodecanoate crosspolymer | — | — | 1% |
| Zeolite | 25% | 25% | 25% |
| PEG-8 | 7.5% | 7.5% | 7.5% |

Examples 18-20

|  | Examples | | |
|---|---|---|---|
| Materials | 18 | 19 | 20 |
| Salicylic acid | 1.5% | 1.5% | 1.5% |
| Butylene glycol | 38.5% | — | — |
| Light mineral oil | — | 59.5% | 45.5% |
| Carrier[1] | — | — | 15% |
| $MgCl_2$ | 35% | 35% | 35% |
| PEG-8 | 5% | — | — |
| polyamide resin | 5% | — | — |
| Polypropylene glycol (PPG)-14 | 15% | — | — |
| Thickener[1] | — | 4% | 3% |

Examples 21-25

|  | Examples | | | | |
|---|---|---|---|---|---|
| Materials | 21 | 22 | 23 | 24 | 25 |
| Salicylic acid | 1.5% | 1.5% | 1.5% | 1.5% | 1.5% |
| Carrier[1] | 27.5% | 15% | 15% | 15% | 15% |
| Thickener[1] | 6% | 2.7% | 8.2% | 3% | 6% |
| Mineral oil | 40% | 45% | 40% | 45% | 42.5% |
| $MgCl_2$[2] | 25% | 35% | 35% | 35% | 35% |
| Fragrance | — | 0.3% | 0.3% | — | — |

Examples 26-28

|  | Examples | | |
|---|---|---|---|
| Materials | 26 | 27 | 28 |
| Salicylic acid | 1.5% | 1.5% | 1.5% |
| Carrier[1] | 15% | 10% | 10% |
| Thickener[1] | — | 2.5% | — |
| Mineral oil | 43.5% | 48.5% | 43.5% |
| Sodium Dodecyl Sulfate | 5% | 2.5% | 10% |
| $MgCl_2$ | 35% | 35% | 35% |

Examples 29-30

|  | Examples | |
|---|---|---|
| Materials | 29 | 30 |
| Salicylic acid | 2% | 2% |
| Carrier[1] | 15% | 30% |
| Mineral oil | 48% | 43% |
| Sodium Dodecyl Sulfate | 5% | 5% |
| $MgCl_2$ | 30% | 20% |

Aqueous Cleansing Compositions

The ingredients listed in each example below were combined by mixing according to conventional methods.

Examples 31-34

|  | Examples | | | |
|---|---|---|---|---|
| Materials | 31 | 32 | 33 | 34 |
| Water | 27% | 20% | 25% | 25% |
| Salicylic acid | 1.5% | 1.5% | 1.5% | 1.5% |
| Butylene glycol | 15% | — | — | — |
| Polyamide resin | 3% | — | — | — |
| Glycerol | — | 25% | 15% | 15% |
| Ethanol | 45% | 45% | 45% | 45% |
| Menthol (L) | 3.5% | — | 3.5% | — |
| Menthol (D/L) | — | 3.5% | — | 3.5% |
| TEA-Laureth Sulphate | — | — | 5% | 5% |
| PEG-8 | 5% | 5% | 5% | 5% |

Examples 35-40

|  | Examples | | | | | |
|---|---|---|---|---|---|---|
| Materials | 35 | 36 | 37 | 38 | 39 | 40 |
| Salicylic acid | 2% | 2% | 2% | 2% | 2% | 2% |
| Butylene glycol | 35% | 30% | 20% | 22% | — | 35% |
| Glycerol | 25% | 20% | 30% | 30% | 40% | 25% |
| PEG-7 glyceryl cocoate | 2.5% | 2.5% | 4% | 3% | 2% | 2% |
| PEG-150 Pentaerythrityl Tetrastearate | 5% | 5% | 4% | 4% | 10% | 3% |
| PEG-8 | 2.5% | 2.5% | 4% | 3% | 2% | 3% |
| polyamide resin | 5% | 15% | 3% | — | — | — |
| PPG-14 butyl ether | — | — | 10% | 13% | 13% | — |
| Water | 13% | 13% | 13% | 3% | 21% | 20% |
| Sodium Lauryl Sulphate (30% in water) | 10% | 10% | 10% | 20% | 10% | — |
| Cocamidopropyl Betaine | — | — | — | — | — | 10% |

Examples 41-44

|  | Examples | | | |
|---|---|---|---|---|
| Materials | 41 | 42 | 43 | 44 |
| Salicylic acid | 2% | 2% | 2% | 2% |
| Butylene glycol | 35% | 35% | 30% | 30% |
| Glycerol | 20% | 20% | 20% | 20% |
| PEG-7 glyceryl cocoate | 2% | 2% | 2% | 2% |
| PEG-8 | 2% | 2% | 2% | 2% |
| Hydrolysed milk protein | 0.2% | 0.2% | 0.2% | 0.2% |
| PPG-14 butyl ether | 10% | 10% | 5% | 6% |
| cocamidopropyl betaine | — | 2.3% | 2.9% | 2.8% |
| Sodium Lauryl Sulphate (30% in water) | 7.5% | 5.3% | 6.7% | 6.7% |
| Lanolin | — | — | 1% | 0.5% |
| Stearyl alcohol | — | — | 2% | 1.5% |
| Sodium Chloride | 1% | 1% | 1% | 1% |
| PEG-150 | — | — | 3% | 3% |
| Water | to 100% | to 100% | to 100% | to 100% |

Examples 45-49

|  | Examples | | | | |
|---|---|---|---|---|---|
| Materials | 45 | 46 | 47 | 48 | 49 |
| Butylene Glycol | 30% | 30% | 30% | 30% | 30% |
| Glycerine | 20% | 20% | 20% | 20% | 20% |
| PEG-7 | 1.5% | 2% | 2% | 2.5% | 2.5% |
| PEG-8 | 1.5% | 2% | 2% | 2.5% | 2.5% |
| PPG-14 | 6.5% | 6.5% | 6.5% | 5% | 5% |
| Lanolin | 2% | 2% | 2% | 2% | 2% |
| Stearyl Alcohol | — | — | — | 0.5% | 1% |
| PEG-150 | 3.5% | 2.5% | 2.5% | 3% | 3% |
| Sodium lauryl sulphate | 6.7% | 6.7% | 6.7% | 6.1% | 6.1% |
| cocamidopropyl betaine | 2.8% | 2.8% | 2.8% | 2.8% | 2.8% |
| NaCl | 1% | 1% | 1% | 1% | 1% |

-continued

| Materials | Examples | | | | |
|---|---|---|---|---|---|
| | 45 | 46 | 47 | 48 | 49 |
| Salicylic Acid | 2% | 2% | 2% | 2% | 2% |
| Hydrolysed Milk Protein | 0.2% | 0.2% | 0.2% | 0.2% | 0.2% |
| Water | to 100% | to 100% | to 100% | to100% | to 100% |

Examples 50-54

| Materials | Examples | | | | |
|---|---|---|---|---|---|
| | 50 | 51 | 52 | 53 | 54 |
| Butylene Glycol | 22.5 | 22.5 | 22.5 | 12.5 | 12.5 |
| Glycerine | 15 | 15 | 15 | 5 | 5 |
| PEG-7 | 2.3 | 2.3 | 2.3 | 2.5 | 2.5 |
| PEG-8 | 2.3 | 2.3 | 2.3 | 1.5 | 1.5 |
| PPG-14 | 3.8 | 3.8 | 3.8 | 3.8 | 3.8 |
| Lanolin | 0.4 | 0.4 | 0.4 | — | — |
| Protanal LF 10/60 | 0.4 | — | — | — | — |
| Carrageenan | — | 0.4 | 1.5 | — | — |
| Carbopol polymer | — | — | — | 1 | 3.8 |
| Crothix Solid | — | — | — | 1.5 | — |
| Sodium lauryl sulphate | 6.5 | 6.5 | 6.5 | 5 | 2 |
| Incronam | 2.1 | 2.1 | 2.1 | 2.1 | 2.1 |
| NaCl | 0.4 | 0.4 | 0.4 | 0.8 | 0.8 |
| Salicylic Acid | 1.5 | 1.5 | 1.5 | 1.5 | 1.5 |
| Hydrolysed Milk Protein | 0.2 | 0.2 | 0.2 | 0.2 | 0.2 |
| Colour | qs | qs | qs | qs | qs |
| Fragrance | qs | qs | qs | qs | qs |
| water | to 100% | to 100% | to 100% | to 100% | to 100% |

Amounts are shown in g.

Examples 55-56

| Materials | Examples | |
|---|---|---|
| | 55 | 56 |
| Butylene Glycol: | 6.0000 | 6.0000 |
| Glycerine: | 3.0000 | 3.0000 |
| PEG-7 | 1.5000 | 1.5000 |
| PEG-8 | 1.5000 | 1.5000 |
| PPG-14 | 3.0000 | 3.0000 |
| S.L.S. | 7.5000 | 6.3750 |
| Arrowroot | 3.0000 | 4.5000 |
| Incronam | 1.0500 | 1.0500 |
| Water: | 44.6250 | 44.2500 |
| Sodium chloride | 0.7500 | 0.7500 |
| Salicylic Acid | 1.5000 | 1.5000 |
| Hydrolysed Milk Protein | 1.5000 | 1.5000 |
| Colour | qs | qs |
| Fragrance | qs | qs |

Examples 57-60

| Materials | Examples | | | |
|---|---|---|---|---|
| | 57 | 58 | 59 | 60 |
| Sodium hydroxide (25%) | 0.86 | 0.86 | 0.34 | 0.8625 |
| Carbopol CC polymer | 3.75 | 3.75 | — | 11.2500 |
| Glycerine | 4.36 | 11.25 | 4.5 | 8.4375 |
| PEG-7 | 1.125 | 1.125 | 13.5 | 0.8438 |
| PEG-8 | 1.125 | 1.125 | 0.15 | 0.8438 |
| S.L.S. (27%) | 7.5 | — | 1.13 | 22.5000 |
| S.D.S solid | — | 15 | 1.13 | — |

-continued

| Materials | Examples | | | |
|---|---|---|---|---|
| | 57 | 58 | 59 | 60 |
| Cocamidopropyl betaine (30%) | 7.5 | — | 11.25 | — |
| Water added | 47.2 | 40.31 | 11.25 | 28.6875 |
| Salicylic Acid | 1.5 | 1.5 | 29.25 | 1.5000 |
| Colour | 0.0002 | 0.0002 | 1.5 | 0.0002 |
| Fragrance | 0.075 | 0.075 | 0.0002 | 0.0750 |

Examples 61-62

| Materials | Examples | |
|---|---|---|
| | 61 | 62 |
| Glycerine | 2.25 | 2.25 |
| Water | 43.67 | 43.67 |
| NaCl | 0.94 | 0.94 |
| Salicylic Acid | 1.5 | 1.5 |
| Hydrolysed Milk Protein | 0.15 | 0.15 |
| Colour | 0.0003 | 0.0003 |
| Fragrance | 0.15 | 0.15 |
| Sodium hydroxide @ 25% | 0.14 | 0.14 |
| Plantacare 818 UP | 6 | 6 |
| Texapon NSO | 20.25 | — |
| Plantapon 611C | — | 20.25 |

Examples 63-64

| Materials | Examples | |
|---|---|---|
| | 63 | 64 |
| Salicylic Acid | 2 | 2 |
| Colour | qs | qs |
| Fragrance | qs | qs |
| Cocoglucoside (50%) | 8 | 8 |
| Glycerin | 2.7 | 2.7 |
| Salt (NaCl) | | 1.2 |
| Sodium Laureth-2 Sulphate (27%) | 52 | 67.7 |
| Levomenthol | 0.1 | — |
| Hydrolysed milk protein | 0.2 | — |
| Sodium chloride | 1.1 | |
| Water | to 100% | to 100% |

Test Method

Skin Preparation:

A sheet of vitro-skin was accurately cut using a guillotine into 10 equal pieces. Each of these pieces was then numbered and weighed before the addition of sebum. Sebum was added to the skin as a solid that could be rubbed across the whole of the skin surface (matte side) until the whole surface was covered (~0.2 g). Each piece of skin was then weighed once more before being placed in the hydration chamber.

The hydration chamber was prepared by adding a mixture of Glycerine (44 g) and DI water (256 g) to the bottom of it. The skin was then placed on the contained shelves and allowed to stand, with the lid tightly in place for approximately 24 hours at ambient conditions in order to ensure a realistic level of vitro-skin hydration.

Cleansing Method

After 24 hours, the lid was removed and cleansing tests were carried out on the skin. For all tests, the vitro-skin was placed on a foam surface to mimic the non-solidity of skin.

For all samples, 5 ml of DI water at room temperature was accurately syringed onto the surface of the vitro-skin. This was then massaged into the skin using a gloved finger with small circular movements for ten seconds. Once this was done the test sample was applied and massaged into the skin.

After cleansing, all skin samples were thoroughly rinsed until for a minimum of 30 seconds, or until all visible products had been removed (as would be the case in a realistic situation).

After cleansing, the vitro-skin was left to dry on the shelves provided in the hydration chamber.

After 24 hours, the skin was then re-weighed providing the information that was required to then calculate the percentage of sebum removed from each piece of vitro-skin.

All testing carried out on vitro-skin was repeated 5 times for each variable.

The test samples were:

A: Water

B: Part 1—Anhydrous composition comprising mineral oil, surfactant, magnesium chloride and salicylic acid (2% w/w) as illustrated herein.

Part 2—Aqueous cleansing composition comprising surfactant and salicylic acid (2% w/w) as illustrated herein.

C: Aqueous cleansing composition comprising surfactant and salicylic acid (2% w/w) as illustrated herein.

The test results were as follows:

|   | Mass of Skin. | Mass of Skin + Sebum | Mass of Skin + Sebum After Cleansing | Mass of Sebum Removed | % Sebum Removed | Average | Standard Deviation | Confidence |
|---|---|---|---|---|---|---|---|---|
| A | 0.601 | 0.798 | 0.705 | 0.093 | 47.2081 | 32.7214 | 12.5944 | 11.039280 |
|   | 0.599 | 0.808 | 0.779 | 0.029 | 13.8756 |   |   |   |
|   | 0.590 | 0.794 | 0.735 | 0.059 | 28.9216 |   |   |   |
|   | 0.568 | 0.762 | 0.697 | 0.065 | 33.5052 |   |   |   |
|   | 0.561 | 0.768 | 0.685 | 0.083 | 40.0966 |   |   |   |
| B | 0.581 | 0.782 | 0.668 | 0.114 | 56.7164 | 78.6322 | 5.29019 | 3.4561965 |
|   | 0.563 | 0.771 | 0.619 | 0.152 | 73.0769 |   |   |   |
|   | 0.565 | 0.754 | 0.608 | 0.146 | 77.2487 |   |   |   |
|   | 0.604 | 0.800 | 0.629 | 0.171 | 87.2449 |   |   |   |
|   | 0.598 | 0.783 | 0.630 | 0.153 | 82.7027 |   |   |   |
|   | 0.463 | 0.661 | 0.515 | 0.146 | 73.7374 |   |   |   |
|   | 0.457 | 0.637 | 0.503 | 0.134 | 74.4444 |   |   |   |
|   | 0.444 | 0.626 | 0.479 | 0.147 | 80.7692 |   |   |   |
|   | 0.467 | 0.679 | 0.522 | 0.157 | 74.0566 |   |   |   |
|   | 0.455 | 0.641 | 0.484 | 0.157 | 84.4086 |   |   |   |
| C | 0.617 | 0.830 | 0.704 | 0.126 | 59.1549 | 44.9166 | 13.0069 | 11.400818 |
|   | 0.580 | 0.790 | 0.670 | 0.120 | 57.1429 |   |   |   |
|   | 0.560 | 0.751 | 0.669 | 0.082 | 42.9319 |   |   |   |
|   | 0.577 | 0.758 | 0.693 | 0.065 | 35.9116 |   |   |   |
|   | 0.552 | 0.749 | 0.691 | 0.058 | 29.4416 |   |   |   |

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. The embodiments of the present invention are also not limited to the particular formulations, process steps, and materials disclosed herein as such formulations, process steps, and materials may vary somewhat. Further, the terminology employed herein is used for the purpose of describing exemplary embodiments only and the terminology is not intended to be limiting since the scope of the various embodiments of the present invention will be limited only by the appended claims and equivalents thereof.

All patents, applications, publications, test methods, literature, and other materials cited herein are hereby incorporated by reference in their entirety as if physically present in this specification.

What is claimed is:

1. A method of treating acne comprising:
   topically administering an acne treating composition to an area of skin exhibiting symptoms of acne, the acne treating composition comprising an acne active ingredient in the presence of an anhydrous composition, wherein the acne active ingredient is selected from the group comprising tretinoin, adapalene, tazarotene, clindamycin, erythromycin, azelaic acid, benzoyl peroxide, hydrogen peroxide and salicylic acid; and
   topically administering an aqueous composition to the area of skin,
   wherein the anhydrous composition further comprises a component that generates heat on the area of skin in the presence of water, said component is selected from the group consisting of magnesium chloride, iron chloride, zinc chloride, magnesium oxide, calcium oxide, magnesium sulphate and calcium chloride.

2. The method according to claim 1, wherein the administration of the anhydrous composition and the aqueous composition is substantially simultaneous.

3. The method according to claim 1, wherein the acne active ingredient is present in the anhydrous composition.

4. The method according to claim 1, wherein the acne active ingredient is present in the aqueous composition.

5. The method according to claim 1, wherein the acne active ingredient is present in an amount of from 0.1% to 10% by weight of the combined anhydrous and aqueous compositions.

6. The method according to claim 1, wherein the acne active ingredient is present in an amount of 0.1% to 5% by weight of the anhydrous composition.

7. The method according to claim 1, wherein the acne active ingredient is present in an amount of 0.1% to 5% by weight of the aqueous composition.

8. The method according to claim 1, wherein the component activatable by water to generate heat on the skin is magnesium chloride.

9. The method according to claim 1, wherein said anhydrous composition comprises from 5% to 60% by weight of said component that generates heat in the presence of water.

10. The method according to claim 1, wherein the anhydrous composition comprises an anhydrous carrier.

11. The method according to claim 10, wherein the anhydrous carrier comprises a hydrocarbon material.

12. The method according to claim 11, wherein the anhydrous carrier comprises mineral oil.

13. The method according to claim 1, wherein the anhydrous composition comprises a surfactant.

14. The method according to claim 13, wherein the surfactant is selected from the group consisting of alkyl sulphates, alkyl ether sulphates, alpha-olefin sulphates, alkylsarcosinates and aryl-sulphonated derivatives thereof.

15. The method according to claim 14, wherein the surfactant is selected from the group consisting of sodium lauryl sulphate and sodium dodecyl sulphate.

16. The method according to claim 13, wherein the anhydrous composition comprises from 1% to 10% by weight surfactant.

17. The method according to claim 1, wherein the aqueous composition is a cleansing composition comprising a surfactant.

18. The method according to claim 1, wherein the aqueous composition is water.

* * * * *